United States Patent [19]

Spiroff

[11] 3,995,518
[45] Dec. 7, 1976

[54] MEANS AND METHODS FOR PUNCHING HOLES IN CATHETERS

[76] Inventor: Carl M. Spiroff, 3117 Davis, Granite City, Ill. 62040

[22] Filed: Aug. 28, 1975

[21] Appl. No.: 608,573

[52] U.S. Cl. .................................... 83/54; 30/358; 83/191
[51] Int. Cl.² ......................................... B26F 1/32
[58] Field of Search .................... 83/54, 185, 191; 30/358, 361, 106

[56] References Cited
UNITED STATES PATENTS

| 200,454 | 2/1878 | Higgins | 83/191 |
|---|---|---|---|
| 672,312 | 4/1901 | Cook | 30/106 |
| 750,746 | 1/1904 | Woodburn | 83/191 |
| 1,432,073 | 10/1922 | Lowy | 83/191 X |
| 1,764,129 | 6/1930 | Trumble et al. | 83/191 |
| 2,116,083 | 5/1938 | Rusch | 83/54 X |

Primary Examiner—Frank T. Yost
Attorney, Agent, or Firm—Joseph A. Fenlon

[57] ABSTRACT

The invention comprises a means and method for punching medically acceptable holes in flexible catheter tubing through a manual punching device which includes an elongated shank sized for snug fitting disposition within the catheter tube and is provided with a pair of cooperating wedge-shaped elements which are driven against each other by manipulation of the device to drive a punch radially outwardly through the wall of the catheter tube and through a complimentary female die which is snugly disposed against the outer wall of the catheter tube.

10 Claims, 14 Drawing Figures

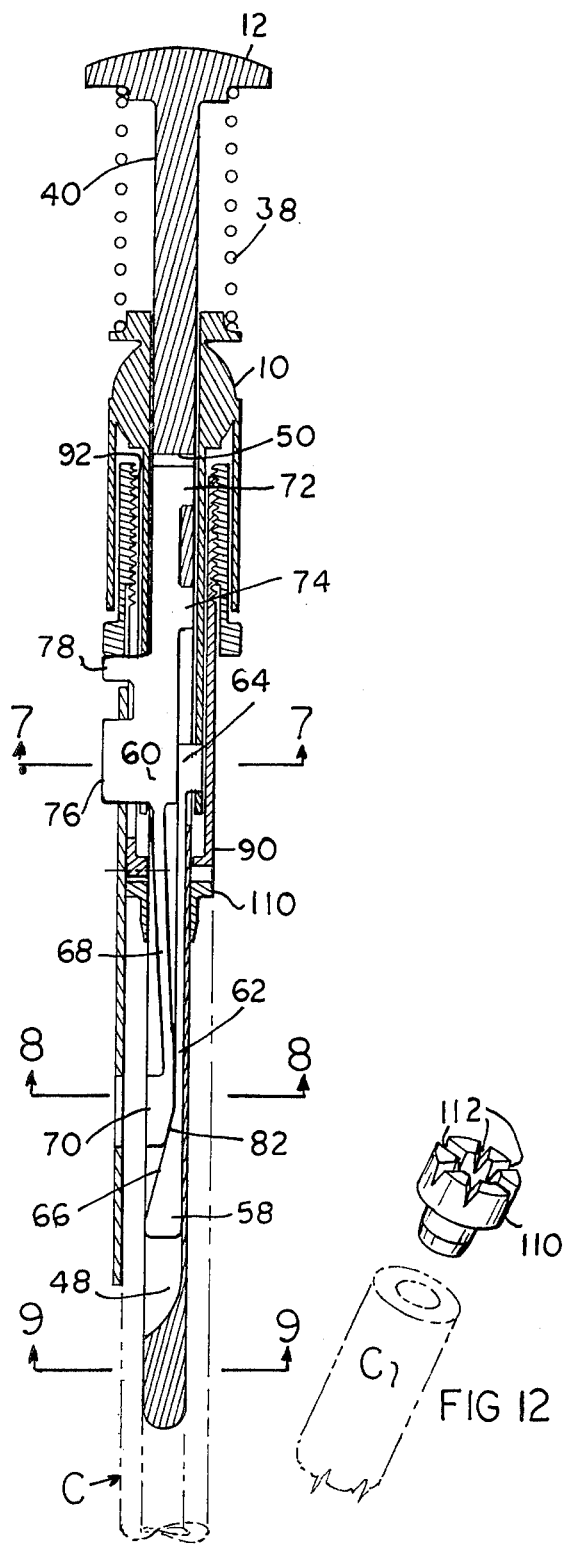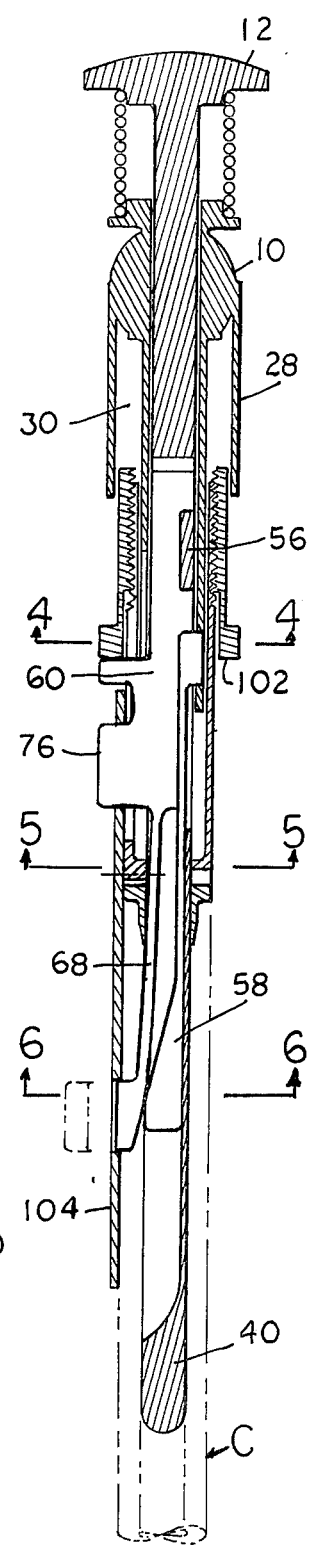

MEANS AND METHODS FOR PUNCHING HOLES IN CATHETERS

The problem with making full utilization of hydraulic principles in catheters has been the inability of present manufacturing techniques and equipment to provide medically acceptable holes in catheters. This difficulty exists because the catheters are small flexible tubes and the normal techniques and equipment used punch the holes from the outside inwardly leaving burrs and rough edges about the holes along the inside wall of the catheter tube which often break loose during usage resulting in moving embolisms in the patient's blood stream.

It is the object of this invention to provide a means and method for forming medically acceptable holes in catheters.

With the above and other objects in view, which will become immediately apparent upon reading this specification, my invention resides in the unique and novel form, construction, arrangement and combination of the various parts and steps shown in the drawings, described in the specification and claimed in the claims.

IN THE DRAWINGS:

FIG. 2 is a sectional view taken along line 2—2 of FIG. 1 with the plunger in the normal position;

FIG. 3 is a sectional view taken along line 2—2 of FIG. 1 with the plunger in the fully depressed position;

Figure 1:
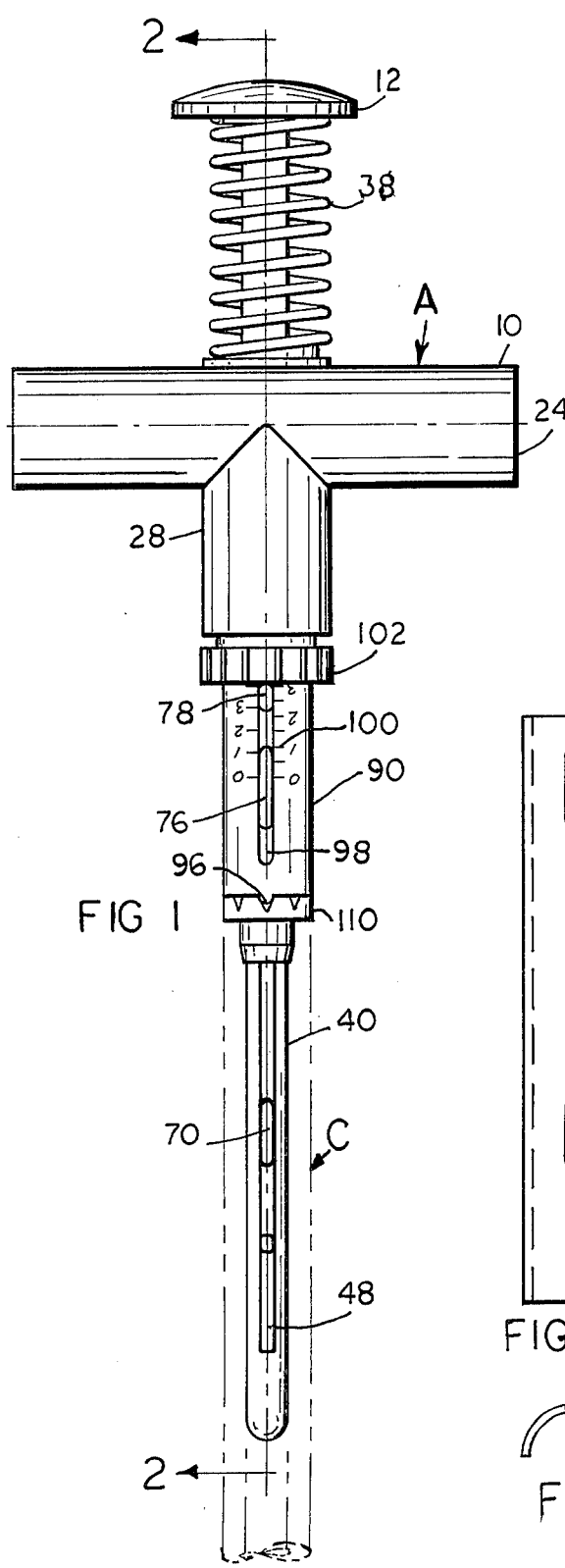
FIG. 1 is a front elevation view of my punching device.
Figure 4:
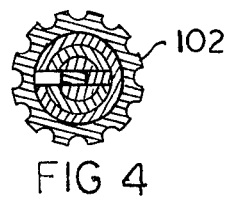
Figure 5:
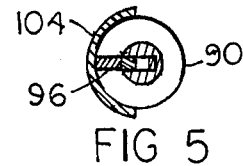
Figure 6:
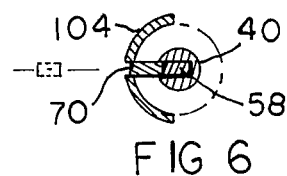
Figure 10:
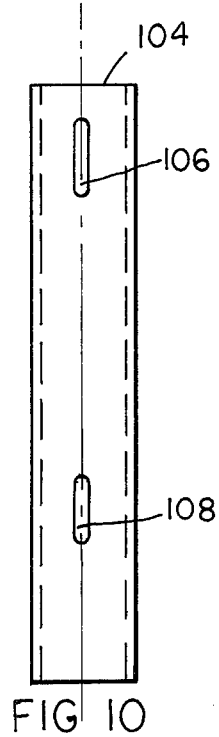
Figure 7:
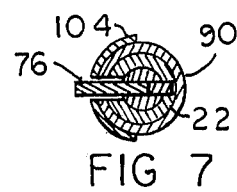
Figure 8:
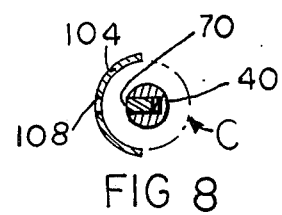
Figure 11:
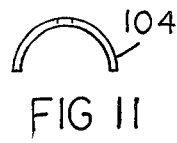
Figure 9:
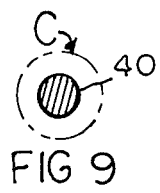
Figure 13:
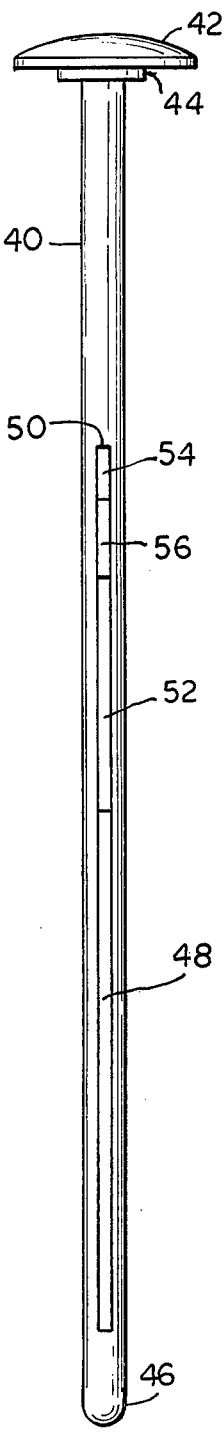

FIGS. 4, 5, and 6 are sectional views taken along lines 4—4, 5—5 and 6—6 respectively of FIG. 3;

FIGS. 7, 8 and 9 are sectional views taken along lines 7—7, 8—8 and 9—9 respectively of FIG. 2;

FIG. 10 is a top plan view of the outer punching die;

FIG. 11 is an end view of FIG. 10;

FIG. 12 is a perspective view of the tubular insert;

FIG. 13 is an elevational view of the punch carrier; and

Figure 14:
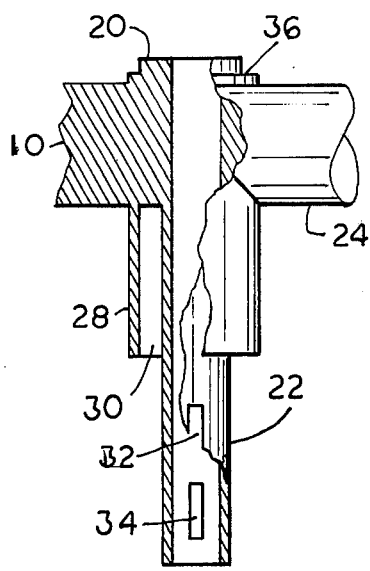

FIG. 14 is a top plan view of the housing with a portion thereof fragmentarily removed.

Referring now in more detail and by reference character to the drawings which illustrate a preferred embodiment of my invention, A designates a Catheter Hole Punch comprising a housing 10 in which is slidably mounted a punch carrier 12.

The housing 10 comprises a T-shaped shell 20 including an elongated cylindrical sleeve 22 and a cross member 24 which is orthogonal to the axis of the sleeve 22. Externally the housing 10 is provided with a depending skirt 28 which extends downwardly from the cross member 24 over a portion of the sleeve 22 to define an annular recess 30 of substantial depth which is coaxial to the axis of the sleeve 22. At the base of the sleeve 22 is an axially extending slot 32 and a diametrally opposed slotted aperture 34, the slot 32 being longer than the aperture 34 and extending upwardly from the base of the leg 22. At its upper end the housing 10 is provided with an annular shoulder 36 adapted for accepting one end of a biasing spring 38.

The punch carrier 12 includes an elongated cylindrical shank 40, diametrally sized for nested disposition in the sleeve 22, and a diametrally enlarged upper end 42 provided with an annular shoulder 44, sized for accepting the other end of the biasing spring 38. Near its lower end 46, the punch carrier 12 is provided with a deep axially extending groove 48 which extends from a point near the end 46 to a face 50.

Near the face 50, the punch carrier 12 is provided with two axially spaced slots 52, 54, which extend the groove 48 completely through the carrier 12 in two spaced places to define a retaining bar 56.

Disposed in the groove 48 in overlapping relationship is a wedge 58 and a punch 60. The wedge 58 comprises a narrow elongated bar 62 terminated at one end with an outwardly projecting ear 64 and at the other end with a ramp section 66 which extends across the depth of the groove 48 as seen in the drawings. The ear 64 is sized for extending through the elongated slot 52 and into snug fitting engagement with the aperture 34. It should be here noted that as assembled the wedge 58 stays fixed with respect to the sleeve 22 when the carrier 12 is moved with respect to the housing 10 because the slot 52 is sized substantially larger than the ear 64.

The punch 60 also comprises an elongated bar 68 provided at one end with a hardened, outwardly extending, rectangular punch die 70 and at the other end with a pair of spaced tabs, 72, 74, sized for overlapping engagement with the slots 52, 54 about the shoulder 56. Intermediate the ends, the punch 60 is provided with a pair of spaced intermediate ears 76, 78, the ear 76 being substantially larger than the ear 78 as seen. The punch 70 is backed by a ramp 82 adapted for sliding cooperation with the ramp section 66 of the wedge 58 as the carrier 12 is moved with respect to the housing 10.

Slidably disposed on the sleeve 22 is a shell 90 which has a threaded upper end 92 and a flat lower end 94 provided with an indexing nub 96. The shell 90 is also provided with an axially extending elongated slot 98 sized for accepting the spaced intermediate ears 76, 78, and provided with an axial displacement scale 100.

Provided for cooperation with the shell 90 is a threaded thumbscrew 102 which cooperates with the threaded end 92 of the shell 90 to position selectively the shell 90 on the sleeve 22 by rotation of the thumbscrew 102. It should be here noted that the ear 78 gives an indication on the displacement scale 100 as to where the punching die 70 is located with respect to the end of the catheter tubing C.

Disposed about the ear 76 and extending downwardly therefrom is a semicylindrical female die 104 provided with a pair of spaced axially extending slots 106, 108, the slot 106 being sized for snugly accepting the ear 76 and the slot 108 being sized for accepting the hardened punch die 70.

The shank 40 of the carrier 12 is diametrally sized for snug fitting disposition in the center of a catheter tube C (shown in phantom) and the female punch die 104 is sized for snug fitting disposition about the outer diameter of the catheter tube C.

Provided for insertion in the end of the catheter tube C to be punched is a tapered insert 110 which is provided with a plurality of equiangularly spaced indexing slots 112 sized for snug fitting engagement about the nub 96 to permit holes to be punched at equally spaced angular intervals about the catheter tube C.

OPERATION

In use, the catheter tube C is placed on the insert 110 and slid onto the shank 40 to where one of the index slots 112 is disposed on the nub 96. In such position, the housing 10 and the carrier 12 are manually urged together against the bias of the spring 38 which causes the wedge 58 to move in the groove 48 against the punch 60 driving the die 70 through the catheter tube C and through the slot 108, thereby causing the tube C to be punched from the inside outwardly. Releasing the carrier 12 and housing 10 forces the wedge die 58 and punch die 60 back to their original position in the groove 48, at which time the insert 110 may be urged away from the nub 96 and a second preselected index slot 112 may be positioned against the nub 96. This process is repeated until the desired number of slots is obtained about the periphery of the tube C at a particular axial location. Since the punching motion has been from the inside outwardly, any sharp edges or small burrs formed by the punching are on the external face of the tubing and may be readily removed by sanding or other common manufacturing techniques such as heat.

If desired, groups of slots may be obtained at different axial positions of the tube C by adjustment the thumbscrew 102 which causes the punch 60 to reposition itself with respect to the wedge 58 in the groove 48. The respective axial positions of the second series of punch holes may be accurately predetermined and regulated by means of the displacement scale 100 on the shell 90.

The punch 60 and female die 104 may alternatively be interchanged with similar dies to provide axially spaced series of different sized holes at different locations in the tube C.

It should be apparent that changes in the form, construction, combination and arrangement of the parts and steps shown herein may be made and substituted without departing from the nature and principle of my invention.

Having thus described my invention what I claim and desire to secure by Letters Patent is recited in the following claims:

1. The method of punching holes in flexible tubing which method comprises
   forming an inner die holder sized for snug-fitting disposition in the hollow portion of the tubing,
   forming an outer die contoured to support the tubing wall firmly against the inner die holder,
   providing the inner die with an elongated channel which extends axially along the tubing axis and which also includes an axially and radially extending ramp,
   locating a die hole in the outer die radially outward from the ramp and in alignment therewith, and
   forcibly urging a male punching die along the channel and up the ramp through the tubing wall and the die hole.

2. A device for punching holes in tubular catheters, which device includes a housing provided with an elongated cylindrical sleeve, an elongated shaft slidably disposed in said sleeve and including an elongated slot, a punching element and a wedge element each slidably disposed in said slot, said elements each being sized and adapted to lie wholly within the slot and each including means for driving the punch element outwardly past the outer margin of the slot when the two elements are moved toward each other within the slot, linkage means for forcibly urging the punching element and the wedge element together in the slot when the shaft is moved with respect to the housing, and biasing means for normally positioning the punching element and the wedge element wholly within the slot, the shaft being perimetrally sized for snug fitting disposition within the catheter tubing whereby the punching element is urged outwardly through the catheter tubing when the shaft is moved with respect to the housing.

3. The device of claim 2 wherein the portion of the shaft which includes the slot is substantially cylindrical.

4. The device of claim 3 wherein the punching element is secured at one end to the shaft and adapted for movement therewith.

5. The device of claim 4 wherein the wedge element is secured at one end to the housing and adapted for movement in the slot when the shaft is moved with respect to the housing.

6. A device for punching holes in catheter tubing, which device comprises a housing provided with manual gripping means at its upper end and an elongated cylindrical sleeve having a retaining slit and a diametrally opposed slot near its lower end,
   a plunger comprising an elongated cylindrical shaft sized for nested disposition in the sleeve of the housing and being provided with an elongated axially extending recess which extends along a substantial portion of said shaft,
   wedging means slidably disposed in said recess and secured to said housing by interlocking means nestedly disposed in said retaining slit,
   and a punching die pivotally disposed in said recess and secured to said plunger for movement therewith, said punching die integrally including a wedge face adapted for sliding movement along the wedge means when the plunger is moved with respect to the housing, said punching die also integrally including a sharp punching face which is moved radially outwardly from said shaft when the wedge face is moved along the wedge means.

7. The device of claim 6 in which the punching die also includes a locating tab which projects through the slot of said sleeve and which is sized for receiving a locating aperture in a female die shaped for snugly supporting the outer wall of the catheter tubing and provided with a punching aperture sized for accepting the punching die, whereby to establish a smooth surface along the sides of the hole punched in the catheter tubing.

8. The device of claim 7 which includes adjustable means for selectively altering the location in the recess where the wedge face engages the wedge means.

9. The device of claim 8 wherein the adjustable means includes a shell mounted on the sleeve for adjustable axial movement with respect thereto, and including an annular face which limits the axial movement of the punching die in the recess.

10. The device of claim 9 in which the shell is provided with an indexing nub and which also includes a tapered insert which is disposed in the end of the catheter tubing about the shaft and which includes a plurality of angularly spaced indexing slots each sized for snugly accepting the nub, whereby a plurality of angularly spaced holes may be preselectively punched in the catheter tubing at substantially the same axial location thereof.

* * * * *